United States Patent [19]

Edwards et al.

[11] 4,046,903

[45] Sept. 6, 1977

[54] ORGANOMETALLIC DERIVATIVES OF PENICILLIN

[76] Inventors: Eva Irene Edwards, 42 Woodfield Avenue, Brierley Hill, West Middlands; Roger Epton, 2 Claydon Road, Wall Heath, West Middlands; George Marr, 67 Swelling Green Lane, Codsal, Wolverhampton, all of England

[21] Appl. No.: 624,405

[22] Filed: Oct. 20, 1975

[30] Foreign Application Priority Data

Oct. 30, 1974 United Kingdom ............... 46932/74
Apr. 29, 1975 United Kingdom ............... 17853/75

[51] Int. Cl.$^2$ .................... C07D 499/44; A61K 31/43
[52] U.S. Cl. ................................. 424/271; 260/239.1
[58] Field of Search ...................... 260/239.1; 424/271

[56] References Cited

PUBLICATIONS

Chemical Abstracts, vol. 74, 3727(f) (French Pat. 2,013,455).

*Primary Examiner*—Gerald A. Schwartz
*Attorney, Agent, or Firm*—Joyce R. Niblack

[57] ABSTRACT

This invention relates to a semi-synthetic penicillin having at least one $\pi$-aromatic, organometallic complex of a transition metal such as ferrocene, attached, preferably in the 6 position, to a penicillin nucleus which optionally carries further substituents.

17 Claims, No Drawings

ORGANOMETALLIC DERIVATIVES OF PENICILLIN

This invention relates to derivatives of penicillin. In particular it is concerned with semi-synthetic penicillins which have metal atom-containing substituents.

Semi-synthetic penicillins have a side chain which normally incorporates a phenyl or heteroaromatic ring. Substitution into this phenyl or heteroaromatic ring will modify the structure of the penicillin essentially in the plane of the aromatic ring. Such substitution may change both the antibiotic activity and the susceptibility to attack by β-lactamase of the penicillin molecule.

While it is desirable to increase the resistance of the penicilin molecule to attack by β-lactamase produced by resistant strains of bacteria with resulting antiobiotic ineffectiveness, this must not be at the expense of a significant reduction in antibiotic activity. Therefore it is an object of the invention to provide a class of semi-synthetic penicillins many of which have good resistance to β-lactamase attack and good antibiotic activity and/or which have modified antibiotic activity and antibiotic spectrum.

According to the invention there is provided a semi-synthetic penicillin having at least one π-aromatic, organometallic complex of a transition metal attached, preferably in the 6-position to a penicillin molecule nucleus which optionally carries further substituents.

We have found that these complex substituents which can have further substituents on the aromatic ring oriented out of the plane of the aromatic ring can improve the stability of the semi-synthetic penicillin to β-lactamase attack without disturbing the molecular profile of the penicillin molecule which is necessary for antibiotic activity. Therefore we can prepare semi-synthetic penicillins of excellent antibiotic activity and good resistance to β-lactamase.

The π-aromatic, organometallic complexes of transition metals are a well knwon and studied group of complexes. They contain one or more rings, each having 3 to 8 carbon atoms, bound to the transition metal. The complex may contain both carbonyl and hydrocarbon groups linked to the metal. Examples of transition metals which form these complexes include iron, manganese, cobalt, and chromium.

Examples of these complexes are:

ferrocene:

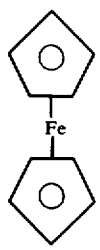

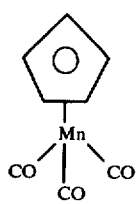

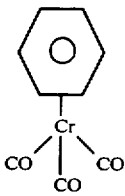

Of these the preferred is ferrocene because of its ready availability and known low-toxicity in view of its use as a medicine to provide an easily metabolised source of iron. Also it is stable and so readily useable in the preparation of the semi-synthetic penicillins of the invention.

The π-aromatic, organometallic complexes are discussed in some detail in the paper "Aromatic complexes of transition metals" by Marr and Rockett in Education in Chemistry, Vol. 9, No. 4, July 1972 to which reference is made.

Where there is a second aromatic ring as in ferrocene, this second or any additional aromatic ring provides a convenient point of attachment for the introduction of substituents which may be particularly effective in β-lactamase inhibition withuout disturbing the conventional molecular profile of the antibiotic necessary for antibiotic activity.

It is believed that this is because, for example, ferrocene is a sandwich compound having the two cyclopentadienyl rings in different planes with the iron atom between them. Thus the second ring which is not linked to the penicillin nucleus will be in an entirely different plane from the pencillin nucleus and it is this second ring which can carry substituents for improving stability. Further the second aromatic ring gives a convenient point of attachment of the synthesis of macromolecular or polymeric derivatives in which the antibiotic activity is preserved.

The semi-synthetic penicillin residue to which the metal complexes can be attached according to the invention has the formula:

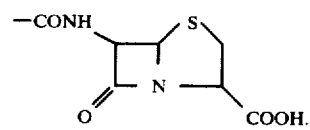

This residue can however contain additional substituents of the type known in the art as substituents for prior semi-synthetic penicillins.

According to one embodiment of the invention, the semi-synthetic penicillin has the general formula:

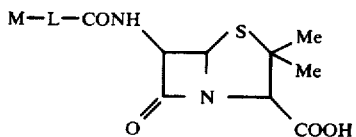

in which L represents a linking group and M the π-aromatic, organometallic complex.

Examples of suitable linking groups are:

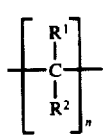 and 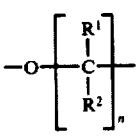

in which $R_1$ and $R_2$, which may be the same as or different from one another, each represents a hydrogen atom or an organic group such as an aryl, alkyl, alkaryl, aralkyl, alkoxy, —CHO, —COOH, —CNH$_2$(CH$_3$)$_2$, —NH$_2$, —C$_6$H$_5$, —CH$_2$SH, —CH$_2$I, —CO—CH$_2$Z where Z is Cl, Br or I, —MeR$_3$ where Me is Si, Ge or Sn and R is a lower alkyl group, e.g. —C$_1$ to C$_4$, and $n$ is 0, 1 or 2, or R$^1$/R$^2$ together with the carbon atom to which they are attached represent the atoms required to complete a carbon ring, e.g. a cyclopropane ring.

Another linking group is:

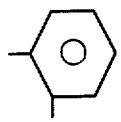

and this benzene ring can be substituted by non-toxic substituents such as those set out below for X and Y.

Examples of particular complexes are:

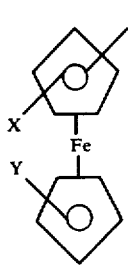 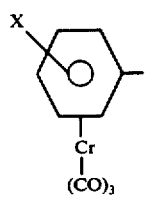 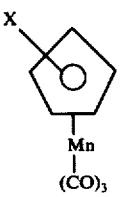

in which X and Y, which may be same as or different from one another, each represents a hydrogen atom, or an organic group, an alkyl, aryl, aralkyl, or alkaryl, any of which may be substituted, a functional organic group such as —CHO, —COOH, —CHN$_2$(CH$_3$)$_2$, —NH$_2$, —C$_6$H$_5$, —CH$_2$SH, —CH$_2$I, or —CO—CH$_2$Z where Z is Cl, Br or I, these organic or organic functional groups being linked directly or indirectly through a divalent carbon chain e.g. methylene or divalent linkage e.g. oxygen the aromatic ring, the group —MeR$_3$ where Me is Si, Ge or Sn and R is a lower alkyl groyp, e.g. C$_1$ to C$_4$, or another penicillin nucleus.

In this latter case one can, for example, prepare a ferrocene-penicillin containing two penicillin residues and having the formula:

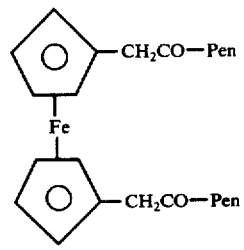

where Pen represents a penicillin residue.

The invention also extends to the pharmaceutically acceptable salts of the semi-synthetic penicillins, e.g. their sodium salts.

Particularly advantageous semi-synthetic penicillins are those on which the organometallic derivative is based on ferrocene since derivatives of this nucleus have minimal toxicity in mammals. Typical compounds of this type are 6-(ferrocenylcarboxamido)penicillanic acid, 6-(2-ferrocenylacetamido)penicillanic acid, 6-(2-ferrocenyl-2-methylacetamido)penicillanic acid, 6-(2-ferrocenyl-2,2-dimethylacetamdio)pencillanic acid, 6-(2-ferrocenyl-2-methoxyacetamido)penicillanic acid, 6-(1-ferrocenylcyclopropanecarboxamido)pencillanic acid, 6-[1-pheny-(o-ferrocenyl)carboxamide]pencillanic acid, 6-(2-ferrocenyloxyacetamido)pencillianic acid, and 1,1'-bis(6-acetamidopenicillanic acid)ferrocene.

The semi-synthetic penicillins of the invention can be prepared in various ways. Thus in most cases the penicillins of the invention can be prepared by the condensation of a carboxylic acid of the complex with a 6-aminopenicillanic acid. This can be achieved by first converting the complex carboxylic acid to its acid chloride, for example, by reaction with phosphorus trichloride under anhydrous conditions at elevated temperatures followed by condensation of the complex acid chloride and the 6-penicillanic acid. In cases where it is not possible to prepare the acid chloride, condensation of the acid with the 6-penicillanic acid may be effected with dicyclohexylcarbodiimide. In either case the condensation can be effected in the presence of an amine such as a teritary amine, e.g. triethylamine.

The semi-synthetic penicillins of the invention are generally prepared in the form of cyrstalline solids which are readily soluble. This can be achieved by combing the condensation product with sodium 2-ethylhexanoate and collecting the sodium salt which separates out. They are therefore relatively easy to prepare, handle and incorporate into pharmaceutical preparations together with conventional pharmaceutically acceptable diluents or other components.

One can also convert one of the semi-synthetic penicillins of the invention to another if the first contains suitable organic functional groups such as those listed in connection with X and Y above. Thus one can attach to those organic functional groups other reactive groups.

The penicillins prepared were isolated as their sodium salts and they can be characterised by the preparation of amine salts. These amines include benzylamine, cyclohexylamine and adamantanamine. The latter was found to be very useful in the characterisation of labile penicillins when other salts could not be isolated as crystalline solids. Therefore the invention extends to the pharmaceutically acceptable salts of the semi-synthetic penicillins described above.

The semi-synthetic penicillins of the invention have good antibiotic activity and so the invention also includes a method of destroying gram-positive and gram-negative bacteria by bringing such bacteria into contact with the semi-synthetic penicillin derivatives according to the invention. A number of the compounds of the invention also provide for the inhibition of penicillin degrading enzymes such as β-lactamase.

The following Preparations and Examples illustrate the preparation of typical starting materials and typical semi-synthetic penicillins of the present invention.

EXAMPLE 1

Preparation of 6-(2-ferrocenylacetamido)penicillanic acid sodium salt

Ferrocenylacetyl chloride (5.25 g) was taken up in 5 cm³ of dichloromethane and added to a mixture of 6-aminopenicillanic acid (4.32 g) and triethylamine (4.04 g) in 65 cm³ of dichloromethane at 2° C. The mixture was stirred for 1 hour at 15° C then filtered, and the filtrate evapoprated cold 'in vacuo'. The residue was dissolved in a mixture of water and ethyl acetate and the aqueous phase adjusted to pH 2.5 with 2M HCl. The phases were then separated and the ethyl acetate phase was washed several times with water, dried and filtered. To the dry ethyl acetate solution was added 8.5 cm³ of a 40% solution of sodium 2-ethylhexanoate in 4-methyl-pentan-2-one. The mixture was concentrated under vacuum and poured into 600 cm³ of dry ether. The yellow solid which separated out was collected by filtration and dried to yield 6.74 g (72%) of the sodium salt. Thin layer chromatography showed the product to be a single substance. The i.r. spectrum showed a strong β-lactam carbonyl absorption at 1760 cm⁻¹ and the p.m.r. spectrum confirmed the structure.

PREPARATION 1

Preparation of 2-ferrocenyl-2-methyl-propionic acid

As suspension of 9.68 g (0.0.38M) of 2-ferrocenyl-2-methyl propanonitrile in 200 cm³ of ethanol was added to a solution of 25 g potassium hydroxide in 200 cm³ of water. The mixture was then brought to reflux. After the evolution of ammonia had ceased (48 h) ethanol was removed 'in vacuo'. The residual suspension was dissolved in 200 cm³ of water, extracted twice with ether and filtered. Acidification of the alkaline solution with 90% orthophosphoric acid afforded a yellow crystalline solid. The product was collected by filtration and dried to yield 7.84 g (76%) of the acid. An analytical sample, melting point 183°-165° C. was obtained by recrystallisation from ethanol/water. (Found C. 61.63; H. 5.85. $C_{14}H_{16}O_2Fe$ requires C, 61.82; H. 5.93%). I.r. and p.m.r. spectra confirmed the structure.

EXAMPLE 2

Preparation of 6-(2-ferrocenyl-2,2-dimethylacetamido) penicillanic acid sodium salt To a solution of 2-ferrocenyl-2-methylpropionic acid (7.55 g) and pyridine (15 drops) in 500 cm³ of dry benzene was slowly added 25 cm³ of phosphorous trichloride. The resulting mixture was stirred for 3 h at 60° to 70° C. After this time the solution was decanted off and the solvent removed under vacuum. The red-brown viscous residue obtained was twice more evaporated from dry benzene to give 6.91 g (85%) of 2-ferrocenyl-2-methylpropanoyl chloride, a red brown solid, which was recrystallised from light petroleum (40° to 60° C).

The ferrocenyl acid chloride (6.91 g) was dissolved in 10 cm³ of dichloromethane and added to a mixture of 6-aminopencillanic acid (5.18 g) and triethylamine (4.85 g) in 100 cm³ of dichloroethane at 2° C. The resulting mixture was stirred for 1 hour at 15° C, filtered and filtrate evaporated cold 'in vacuo'. the residue was dissolved in a mixture of water and ethyl acetate and the aqueous phase adjusted to ph 2.5 with 2M HCl. The phases were separated and the aqueous phase extracted with ethyl acetate. The combined extracts of ethyl acetate were washed several times with water, dried and filtered. To the dry ethyl acetate solution was added 10 cm³ of a 40% solution of sodium 2-ethylhexanoate in 4-methylpentan-2-one. The mixture was concentrated under vacuum and then poured into 600 cm³ of dry ether. The product, which separated as a pale yellow solid, was collected by filtration and dried to yield 8.43 g (72%) of the penicllin. The i.r. spectrum showed a stron β-lactam carbonyl absorption at 1760 cm⁻¹. A thin layer silica gel chromatogram (chloroform/acetone/acetic acid) showed a single substance.

PREPARATION 2

Preparation of (ferrocenyl)(methoxy)acetic acid

To a solution of potassium hydroxide (5g) in 60cm³ of water was added a suspension of (ferrocenyl)methoxy)-acetonitrile (2.2 g) in 25 cm³ of ethanol. The mixture was brought to reflux and after the evolution of ammonia had ceased (60h) ethanol was removed 'in vacuo'. The residual suspension was dissolved in 200 cm³ of water, extracted twice with ether and filtered. Acidification of the alkaline solution with 90% phosphoric acid gave the product, a yellow solid. This was collected by filtration and dried to yield 1.78 g (75%) of (ferrocenyl)-(methoxy)acetic acid, melting point 100° to 102° C. This mass spectrum had a parent peak at m/e 274 ($C_{13}H_{14}FeO_3$ calcd: 174.10). The i.r. spectrum showed a strong acid carbonyl absorption at 1710 cm⁻¹ and the p.m.r. spectrum exhibited resonances at 4.67 (S. C$\underline{H}$), 4.21 (S, ring protons), and 3.48 (S,OCH₃) ppm.

EXAMPLE 3

Preparation of 6-(2-ferrocenyl-2-methoxyacetamido) penicillanic sodium salt

A mixture of (ferrocenyl)(methoxy)acetic acid (1.37 g) and dicyclohexycarbodiimide (1.03 g) was dissolved in 40 cm³ of dichloromethane, and the solution stirred for 1 hour at room temperature. To this solution was then added a mixture of 6-aminopenicillanic acid (1.08g) and triethylamine (0.51 g) in 20 cm³ of dichloromethane. The resulting mixture was stirred for 2 hours at room temperature, filtered and the filtrate evaporated cold 'in vacuo'. The residue was dissolved in a mixture of water and ethyl acetate and the aqueous phase adjusted to pH 2.5 with 2M HCl. The phases were separated and the ethyl acetate phase washed with water, dried and filtered. To the dry ethyl acetate solution was added 2 cm³ of a 40% solution of sodium 2-ethylhexanoate in 4-methyl-pentan-2-one. The mixture was concentrated under vacuum and poured into 100 cm³ of dry ether. The sodium salt was obtained as a 'tacky' brown solid in low yield, 0.29 g (12.4%) and proved to be very labile.

EXAMPLE 4

Preparation of the adamantanamine salt of 6-(2-ferrocenyl-2-methoxyacetamido)penicllanic acid Since the sodium salt of 6-(2-ferrocenyl-2-methoxyacetamido)penicillanic acid proved to be labile, the penicillin was characterised by the preparation of the adamantanamine salt. The sodium salt (0.2 g) was dissolved in 100 cm³ of water and the solution layered with 50 cm³ of ether. After adjusting the aqueous layer to pH 2.5 with 2M HCl, the two phases were separated. The ethereal layer was washed well with water, dried, filtered and to it was added an ethereal solution of adamantanamine. The salt separated out immediately, was collected by filtration and dried under vacuum to give 0.12 g (50%) of a stable, highly crystalline solid, melting point 157° to 159° C with decomposition. (Found C, 59.99; H, 7.11; $C_{31}H_{41}FeN_3O_5S$ requires C, 59.71; H 6.63%). The i.r. spectrum showed a strong β-lactam carbonyl absorption at 1775 cm⁻¹ and the p.m.r. spectrum confirmed the structure.

EXAMPLE 5

Preparation of 6-[1-phenyl-(o-ferrocenylbenzoic acid]penicillanicc acid sodium salt To a solution of o-ferrocenylbenzoic acid (1.75 g) and pyridine (3 drops) in 10 cm³ of dry benzene was slowly added 5 cm³ of phosphorous trichloride. The resulting mixture was then stirred for 3 hours at 60° to 70° C. After this time the solution was decanted off and the solvent removed under vacuum. The residue was twice more evaporated from dry benzene and then taken up in light petroleum (40° to 60°). Removal of the solvent under vacuum afforded 1.54 g (83%) of o-ferrocenylbenzoyl chloride, a dark-red, viscous oil.

The o-ferrocenylbenzoyl chloride (1.54 g) was dissolved in 5 cm³ of dichloromethane and added dropwise to a mixture of 5-aminopenicillanic acid (1.01 g) and triethylamine (0.95 g) in 20 cm³ of dichloromethane at 2° C. The reaction mixture was stirred for 1 hour at 15° C, then filtered and the filtrate evaporated 'in vacuo' at room temperature. A mixture of 100 cm³ of water and 50 cm³ of ethyl acetate was added to the residue and the aqueous phase adjusted to a pH of 2.5 with 2M hydrochloric acid. The phases were then separated and the aqueous phase extracted with ethyl acetate. The combined extracts of ethyl acetate were washed several times with water, dried and filtered. To the dry ethyl acetate solution was added 2 cm³ of a 40% solution of sodium 2-ethylhexanoate in 4-methylpentan-2-one. The resulting mixture was concentrated under vacuum and then poured into 100 cm³ of dry ether. The product, which separated as a yellow amorphous solid, was collected by filtration and dried to yield 1.34 g (54%) of sodium 6-[1-phenyl-)o-ferrocenyl) carboxamido pencicillanic]carboxylate.

EXAMPLE 6

Preparation of 6-(ferrocenylcarboxamido)penicillanic acid (sodium salt)

Ferrcenoyl chloride (0.85g, 0.0034 m) was dissolved in dichloromethane (10 cm³) and added dropwise to a mixture of 6-aminopenicillanic acid (0.73 g, 0.0034 m) and triethylamine (0.69 g, 0.0068 m) in dichloromethane (16 cm³) at 2° C. The mixture was stirred for 1 hour at 15° C then filtered and the filtrate evaporated under vacuum at room temperature. The residue was dissolved in a mixture of water (50 cm³) and ethyl acetate (25 cm³) and the aqueous layer adjusted to pH 2.5 with 2M HCl. The ethyl acetate layer was washed with water, dried (Mg SO₄), filtered and a 40% solution of sodium 2-ethyl-hexanoate in 4-methylpentan-2-one (1cm³) added. The mixture was concentrated under vacuum and added dropwise to 150 cm³ of dry light petroleum (40° to 60°). The sodium salt of 6-(ferrocenylcarboxamido) penicillin which separated out was collected by filtration and dried to yield 0.88 g (58%). The i.r. spectrum showed a β-lactam carbonyl absorption at 1765 cm⁻¹.

EXAMPLE 7

Preparation of 6-(2-ferrocenyl-2-methylacetamido) penicillanic acid (sodium salt)

To a mixture of 6-aminopenicillanic acid (1.56 g, 0.0165 m) and triethylamine (3.33 g, 0.033 m) in dichloromethane (50 cm³) at 2° C was added dropwise a solution of 2-ferrocenyl-propanoyl chloride (4.56 g, 0.0165 m) in dichloromethane (5 cm³). The mixture was stirred for 1 hour at 15° C, filtered and the solvent removed under vacuum at room temperature. To the residue was added a mixture of water (100 cm³) and ethyl acetate (50 cm³) and the aqueous layer was then adjusted to pH 2.5 with 2M HCl. The layers were separated and the organic phase washed with water, dried, filtered and a 40% solution of sodium 2-ethyl-hexanoate in 4-methylpentan-2-one (5.3 cm³) added. The mixture was concentrated under vacuum and then poured into dry ether (500 cm³). The sodium salt of the penicillin separated out as a pale yellow solid. This was washed by decanatation with ether, collected by filtration and dried to give 2.7 g (50%) of product. The i.r. spectrum showed a strong β-lactam carbonyl absorption at 1750 cm⁻¹ and the product was shown to be pure by thin layer chromatography.

PREPARATION 3

Preparation fof ferrocenyl-cyclopropane carboxylic acid

To a solution of potassoum hydroxide (8 g) in water 80cm³) was added a suspension of 1-ferrocenyl-1-cyanocyclopropane (3.7 g, 0.0147 m) in ethanol (35 cm³) and the mixure brought to reflux. When the evolution of ammonia had ceased (48 hours) the ethanol was removed 'in vacuo' and the residual suspension dissolved in water (100 cm³). The aqueous solution was washed with ether and filtered. Acidification of the alkaline solution with 90% orthophosphoric acid afforded 3.32 g (83%) of a yellow crystalline solid, m.p. 172°-174° C. I.r., p.m.r. and mass spectrometry confirmed the structure.

EXAMPLE 8

Preparation of 6-(1-ferrocenylcyclopropanecarboxamide) penicillanic acid (sodium salt)

Phosphorous III chloride (4.5 cm³) was added dropwise to a solution of ferrocenyl-cyclopropane carboxylic acid (1.35 g, 0.005 m) and pyridine (3 drops) in dry benzene (90 cm³). The mixture was stirred for 3 hours at 60° to 70° C. The benzene solution was then decanted off and the solvent removed under vacuum. The residue was dissolved in benzene and the benzene evaporated. This procedure was repeated. Recrystallisation from light petroleum (40° to 60°) afforded 1.17 g (81%) of ferrocenylcyclopropanol chloride as a deep yellow crystalline solid.

The ferrocenyl acid chloride (0.86 g, 0.003 m) was dissolved in 5 cm³ of dichloromethane and added dropwise to a mixture of 6-aminopenicillanic acid (0.65 g, 0.003 m) and triethylamine (0.61 g, 0.006 m) in dichloromethane (20 cm³) at 0° C. The mixture was stirred for 15 minutes at 0° C and 1 hour at 15° C then filtered and the solvent removed under vacuum at room temperature. The residue was taken up in a mixture of water (100 cm³) and ethyl acetate (25 cm³) and the aqueous layer adjusted to pH 2.5 with 2M HCl. Layers separated and the ethyl acetate layer washed with water, dried (MgSO₄), filtered and a 40% solution of SEH in 4-methylpentan-2-ine (1.25 cm³) added. The mixture was concentrated under vacuum and then added dropwise to dry ether (200 cm³). The sodium salt separated out as a pale yellow solid and was collected by filtration and dried to yield 1.08 g (73%) of 6-(1-ferrocenylcyclopropane-carboxamido)penicillin. Thin layer chromatography showed the product to be pure and the i.r. spectrum showed a strong β-lactam carbonyl absorption at 1765 cm⁻¹.

EXAMPLE 9

Preparation of 6-(2-ferrocenyloxyacetamido)penicillanic acid (sodium salt)

To ferrocenyloxyacetic acid (1.56 g, 0.006 m) and pyridine (4 drops) in benzene (100 cm³) was added dropwise phosphorous (III) chloride (5.4 cm³). The mixture was stirred for 3 hours at 60° to 70° C. After this time the benzene solution was decanted and the benzene removed under vacuum. The residue was taken up in benzene and the benzene again removed under vacuum. This procedure was repeated. Recrystallization from light petroleum (40° to 60°) gave 1.40 g (83.8%) of ferrocenyloxyacetyl chloride. The chloride (1.40g, 0.005 m) was taken up in dichloromethane (5cm³) and added dropwise to a mixture of 6-aminopenicillanic acid (1.08 g, 0.005 m) and triethylamine (1.01 g, 0.0 m) in dichloromethane (25 cm³) at 0° C. The mixture was stirred for 15 minutes at 0° C and for 1 hour at 15° C. The solution was then filtered and the solvent removed under vacuum. The residue was taken up in a mixture of water (100 cm³) and ethyl acetate (25 cm³) and the aqueous layer adjusted to pH 2.5 with 2M HCl. The layers were separated and the ethyl acetate layer washed with water, dried, filtered and a 40% solution of SEH in 4-methylpentan-2-one (2 cm³) added. Worked up as previously the yield was 1.53 (67%) of the sodium salt of 6-(2-ferrocenyloxyacetamido) penicillanic acid. I.r. spectrum showed strong β-lactam absorption at 1770 cm⁻¹.

EXAMPLE 10

Preparation of 1,1'-bis(6-acetamidopenicillanic acid) ferrocene

To a solution of 1,1'-ferrocenediacetic acid (3.02 g, 0.01 m) and pyridine (10 drops) in benzene (200 cm³) was added dropwise phosphorous (III) chloride (20 cm³). Procedure as previously but acid chloride recrystallised from benzene. Yield 2.01 g (60%) — crystalline solid.

1,1'-ferrocenediacetyl chloride (2 g, 0.006 m) in dichloromethane (10 cm³) added dropwise to mixture of 6-aminopenicillanic acid (2.6 g, 0.012 m) and triethylamine (2.42 g, 0.024 m) in dichloromethane (30 cm³) at 0° C. Mixture stirred for 15 minutes at 0° C and 1 hour at 15° C. Procedure as for previous penicillins. Yield of sodium salt of 1,1'-bis(6-acetamido-penicillanic acid)ferrocene was 2.63 g (59%).

PURIFICATION

The sodium salt was dissolved in water and the aqueous solution adjusted to ph 2.5 with 2M HCl. The free penicillanic acid, which was deposited as a 'tacky' solid, was washed with water and ether and taken up in acetone. To the acetone solution was added a solution of sodium 2-ethyl-hexanoate in acetone. The sodium salt of the penicillin which separated out was washed by decantation with acetone, collected by filtration and dried. The i.r. spectrum showed strong β-lactam absorption at 1765 cm⁻¹.

EXAMPLE 11

Preparation of 1-[6-(o-phenylcarboxamido)penicillanic acid]-1'-(methoxymethyl)ferrocene (sodium salt)

A mixture of 1-(o-phenylcarboxylic acid)-1'-(methoxymethyl)ferrocene (1.75 g, 0.005 m) and N,N'-dicyclohexylcarbodiimide (1.03 g, 0.005 m) in dichloromethane (25 cm³) was stirred at room temperature for 2 hours. To the mixture was added a suspensiion of 6-aminopenicillanic acid (1.08 g, 0.005 m) and triethylamine (0.51 g, 0.005 m) in dichloromethane (15 cm³). The reaction mixture was stirred for a further 48 hours at room temperature. The percipitated dicyclohexylurea was removed by filtration and the filtrate evaporated under vacuum at room temperature. The residue was dissolved in a mixture of water (150 cm³) and ethyl acetate (50 cm³) and the layers separated. The aqueous solution was again layered with ethyl acetate (50 cm³) and adjusted to pH 2.5 with 2MHCl. The layers were separated and they ethyl acetate layer was washed with water, dried (MgSO₄), filtered and a 40% solution of sodium 2-ethylhexanoate in 4-methylpentan-2-one (2 cm³) added. The mixture was concentrated under vacuum and added dropwise to dry ether (250 cm³). The sodium salt of 1-[6-(o-phenylcarboxamido)penicillanic acid]-1'-(methoxymethyl) ferrocene, which separated as a deep yellow solid, was washed by decantation with ether and collected by filtration (0.568 g, 20%). The salt exhibited the required i.r. and p.m.r. data.

PREPARATION 4

Preparation of 1-acetylchloride-2-trimethylsilyl ferrocene

To a solution of 1-methylcarboxylic acid 2-trimethylsilyl ferrocene (1.1 g, 0.0039M) and pyridine (3 drops) in dry benzene (100 cm³) was added phosphorus (III) chloride (6 cm³) with stirring. The mixture was stirred for 3 hours at 60° to 70° C. The resulting solution was decanted off and the volume reduced under vacuum to give a red oil. The red oil was dissolved in dry benzene and the solvent removed under vacuum. This procedure was repeated and a red oil was obtained.

The product was extracted with dry petroleum ether boiling point 40° to 60° filtered and the solution evaporated to give 1-acetyl chloride-2-trimethylsilyl ferrocene (0.9 g).

EXAMPLE 12

Preparation of sodium salt of 1-acetyl-2-trimethyl silyl ferrocene penicillanic acid To a solution of 5-amino penicillanic acid (1.2 g, 0.0057 m) and triethylamine (1.12 g, 0.011 m) in dichloromethane (20 cm³) was added slowly 1-acetyl chloride 2-trimethyl silyl ferrocene (1.62 g, 0.00513 m) in dichloromethane (10 cm³) at 2° C. The mixture was stirred for 1 hour at 15° C, filtered and the solvent evaporated under vacuum in the cold to give a yellow solid. Water (50 cm³) and ethyl acetate (50 cm³) were added to the solid and the pH of the aqueous layer adjusted to 2.5 with 2M hydrochloric acid.

The layers were separated and the aqueous layer extracted once with ethyl acetate. The combined ethyl acetate layers were washed twice with water, dried (MgSO₄), filtered and sodium 2-ethyl hexanoate (0.92g) in 4-methylpentan-2-one (2.2 cm³) added. The resultant mixture was concentrated under vacuum and added to dry ether (100 cm³) when a yellow precipitate separated. This precipitate was collected by filtration, washed with dry ether and dried under vacuum. (yield 0.94 g, m.pt. decomposes 140° C).

EXAMPLE 13

Preparation of the adamantamine salt of 1-[6-(acetamido) penicillanic acid]-2-trimethyl silyl ferrocene The sodium salt of 1-[6-(acetamido)penicillanic acid]2-trimethyl silyl ferrocene (0.2 g) was added to water (50 cm³), this solution layered with ether (50 cm³) and the pH adjusted to 2.5. The layers were separated and the aqueous layer extracted with ether. The ether extracts were dried (MgsO₄) and filtered. To this solution of the free acid was added a 10% solution of adamantamine in ether (molar amount). The solution was evaporated to give a yellow solid of the adamantamine salt of 1[6-(acetamido)penicillanic acid]-2-trimethyl silyl ferrocene. yield 0.12 g., m.pt decomposes 140° C. (Found C 60.17; H 7.73 $C_{33}H_{47}SiFeN_3SO_4$ requires C 59.56; H 7.07.)

What we claim is:

1. A semi-synthetic penicillin of the formula:

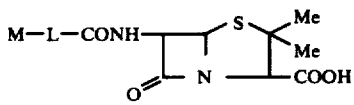

wherein: L is selected from the group consisting of

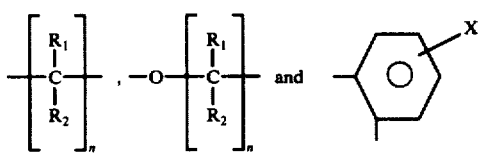

$n$ being an integer from 0 to 2, and each $R_1$ and $R_2$ are the same or different members of the group consisting of hydrogen, alkyl, aryl, alkaryl, aralkyl, alkoxy, —CHO, —COOH, —CH₂N(CH₃)₂, —NH₂, —C₆H₅, —CH₂SH, —CH₂I, —CO—CH₂Z wherein Z is Cl, Br or I, —MeR₃ wherein Me is Si, Ge or Sn and R is alkyl containing 1 to 3 carbon atoms, or $R_1$ and $R_2$ taken together form a cycloalkyl group; and M is selected from the group consisting of pi-bonded aromatic organometallic complexes of a transition metal represented by the formulae:

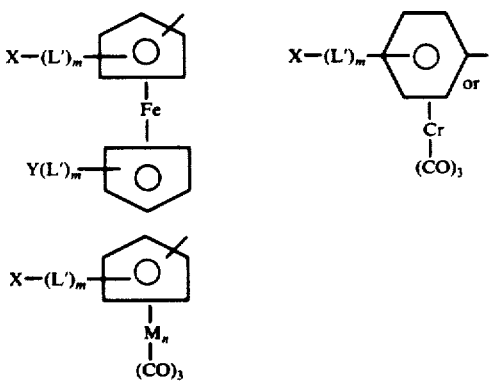

X and Y being the same of different members of the group consisting of hydrogen, alkyl, aryl, aralkyl, alkaryl, —CHO, —COOH, —CH₂N(CH₃)₂, —NH₂, —C₆H₅, —CH₂SH, —CH I or —CO—CH₂Z wherein Z is Cl, Br or I, —MeR₃ wherein Me is defined as above, or another penicillin nucleus:

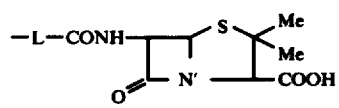

L' represents a methylene linkage or —O—, and $m$ is 0 or 1, or a pharmaceutically acceptable salt thereof.

2. A semi-synthetic penicillin in accordance with claim 1 wherein each $R_1$ and $R_2$ are the same or different members of the group consisting of hydrogen, $C_1$-$C_3$ alkyl, phenyl, benzyl, $C_1$-$C_3$ alkoxy, —CHO, COOH, —CH₂N(CH₃)₂, —NH₂, —C₆H₅, —CHSH, —CH₂I, —CO—CH₂Z wheirein Z is Cl, Br or I, —MeR₃ wherein Me is Si, Ge or Sn and R is $C_1$-$C_3$ alkyl, or $R_1$ and $R_2$ taken together form a $C_3$-$C_8$ cycloalkyl group; and M is ferrocene.

3. A semi-synthetic penicillin in accordance with claim 2 wherein L is phenyl.

4. A semi-synthetic penicillin in accordance with claim 1 wherein L is phenyl.

5. A semi-synthetic penicillin in accordance with claim 1 wherein M is represented by the formula

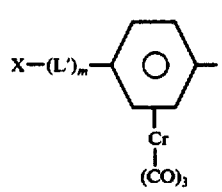

where X is hydrogen and $m$ is 0.

6. A semi-synthetic penicillin in accordance with claim 1 wherein M is

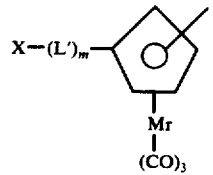

where X is hydrogen and $m$ is 0.

7. 6-(Ferrocenylcarboxamido)penicillanic acid.
8. 6-(2-Ferrocenylacetamido)penicillanic acid.
9. 6-(2-Ferrocenyl-2-methylacetamido)pencillanic acid.
10. 6-(2-Ferrocenyl-2,2-dimethylacetamido)pencillanic acid.
11. 6-(2-Ferrocenyl-2-methoxyacetamido)penicillanic acid.
12. 6-(1-Ferrocenylcyclopropanecarboxamido)penicillanic acid.
13. 6-[1-Phenyl-(o-ferrocenyl)carboxamido]penicillanic acid.
14. 6-(2-Ferrocenyloxyacetamido)penicillanic acid.
15. 1,1'-Bis(6-acetamidopenicillanic acid)ferrocene.
16. A pharmaceutical composition comprising a therapeutically effective amount of a semi-sythetic penicillin in accordance with claim 1 and a pharmaceutically acceptable carrier or diluent.
17. A method of treating bacterial infections comprising administering a therapeutically effective amount of a semi-synthetic penicillin of claim 1, or a pharmaceutically acceptable salt thereof, to a mammalian host in need of such treatment.